(12) United States Patent
Frustaci et al.

(10) Patent No.: US 6,613,474 B2
(45) Date of Patent: Sep. 2, 2003

(54) ELECTROCHEMICAL CELL HAVING A CASING OF MATING PORTIONS

(75) Inventors: Dominick Frustaci, Williamsville, NY (US); Kenneth Grubb, Snyder, NY (US); Paul Hallifax, Gasport, NY (US); William M. Paulot, Lancaster, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 118 days.

(21) Appl. No.: 09/757,232

(22) Filed: Jan. 9, 2001

(65) Prior Publication Data

US 2001/0049057 A1 Dec. 6, 2001

Related U.S. Application Data

(60) Provisional application No. 60/195,007, filed on Apr. 6, 2000.

(51) Int. Cl.[7] .................................................. H01M 2/00
(52) U.S. Cl. ........................ 429/163; 429/185; 429/176
(58) Field of Search ................................ 429/176, 162, 429/163, 185

(56) References Cited

U.S. PATENT DOCUMENTS

| | | | |
|---|---|---|---|
| 2,861,117 A | * 11/1958 | Sindel | 429/162 |
| 4,659,636 A | 4/1987 | Suzuki et al. | 429/54 |
| 5,270,133 A | 12/1993 | Baumann, III | 429/53 |
| 5,288,565 A | * 2/1994 | Gruenstern | 429/152 |
| 5,750,286 A | 5/1998 | Paulot et al. | 429/211 |
| 5,926,362 A | 7/1999 | Muffoletto et al. | |
| 5,958,088 A | 9/1999 | Vu et al. | |
| 6,004,692 A | 12/1999 | Muffoletto et al. | 429/163 |
| 6,004,693 A | 12/1999 | Fukuda et al. | 429/176 |
| 6,040,084 A | * 3/2000 | Kurasawa et al. | 429/163 |
| 6,048,642 A | * 4/2000 | Woolsey | 429/100 |
| 6,117,195 A | 9/2000 | Honegger | 29/623.2 |
| 6,265,102 B1 | * 7/2001 | Shrim et al. | 429/163 |
| 6,334,879 B1 | 1/2002 | Muffoletto et al. | |
| 6,445,948 B1 | 9/2002 | Somdahl et al. | |
| 6,498,951 B1 | * 12/2002 | Larson et al. | 607/36 |
| 2003/0040781 A1 | 2/2003 | Larson et al. | |

FOREIGN PATENT DOCUMENTS

| | | |
|---|---|---|
| EP | 0928035 A1 | 7/1999 |
| GB | 1468120 | 3/1997 |
| JP | 06181069 | 6/1994 |
| JP | 10199493 | 7/1998 |
| WO | WO 01/82393 A2 | 11/2001 |

OTHER PUBLICATIONS http://headwize2.powerpill.org/projects/showproj.php?file=cmoy2a_add_prj.htm.*

* cited by examiner

*Primary Examiner*—Carol Chaney
(74) *Attorney, Agent, or Firm*—Michael F. Scalise (57) ABSTRACT

The present invention is directed to an electrochemical cell having plate electrodes housed inside mating "clam shell" casing components. Also, the present casing design allows for indentation structures in the casing components by virtue of them being stamped metal parts. Such indentations are not possible with traditional cylindrical and prismatic casing designs. When mated together, the casing components are form-fitting with respect to the internal battery structure so as to reduce the overall size of the electrochemical package. This provides the cell with the greatest amount of energy per unit size.

37 Claims, 7 Drawing Sheets

ELECTROCHEMICAL CELL HAVING A CASING OF MATING PORTIONS

CROSS-REFERENCE TO RELATED APPLICATION

The present application claims priority based on provisional application Ser. No. 60/195,007, filed Apr. 6, 2000.

BACKGROUND OF THE INVENTION

1. Field of the Invention

The present invention relates to an electrochemical cell designed for improving energy density by forming a prismatic case of at least two stamped metal components mated to reduce cell size. More particularly, the present invention relates to an electrochemical cell housed in a casing of mated stamped metal halves that may have a recess or indentation provided in the body of at least one of the casing components.

2. Prior Art

Lithium anode based electrochemical cells, such as silver vanadium oxide cells used in implantable medical device applications, are typically housed in cylindrical and prismatic casings. Both of these housing designs comprise two main components, a lid and a deep drawn case.

For example, the prior art reveals U.S. Pat. No. 6,004,692 to Muffoletto et al., assigned to the assignee of the present invention and incorporated herein by cell housed in a prismatic casing enclosure for lithium electrochemical cell. The cell includes a deep drawn conductive casing having an open end closed by a connected lid. The lid is provided with a terminal pin serving as a lead for making electrical connection to a load. The casing itself provides the other terminal for the cell. The generally prismatic or rectangular shape of the Muffoletto et al. casing makes it extremely difficult, if not impossible, to provide indentations or recesses in the casing side wall while simultaneously inserting a cell stack with the case in an efficient manner. Such recesses are useful for nesting components of the device being powered by the cell.

The use of casing halves constructed of resin materials is also known in the prior art. For example, U.S. Pat. No. 4,659,636 to Suzuki et al. relates to a sealed storage battery housed inside casing halves molded from a synthetic resin. A suitable synthetic material is a composition containing blended ABS and polycarbonate resins.

Also, dipping battery elements in liquid thermoplastic encapsulating materials has been described. For example, U.S. Pat. No. 5,270,133 to Baumann III describes a case-less battery wherein the electrode elements are housed in an encapsulating material. The electrode elements are encapsulated by dipping them into air or heat curable thermoplastic materials.

Also, the use of a sealing bag in a non-aqueous electrolyte battery is known. For example, U.S. Pat. No. 6,404,693 to Fukuda et al. describes a non-aqueous electrolyte cell having electrode elements house in a sealing bag whose peripheral parts are heat fused together. The sealing bag is formed from a film having a multilayered configuration including a metal layer (metal foil) and an electrolytic solution insulating barrier layer.

The problem with the prior art constructions is that synthetic materials are not suitable for providing a hermetic enclosure, especially for an electrochemical cell intended to power an implantable medical device. Also, a prismatic or cylindrically-shaped casing may not be acceptable in all instances, for example in batteries powering implantable medical devices where it is desirable to have an indentation in the body of the casing for nesting components of the medical device. What is needed is a new casing construction of stamped metal components which allows for greater flexibility in package shape than is offered by traditional designs. These battery cases permit the cell designs to be much more flexible in nature while allowing for extremely energy efficient designs.

SUMMARY OF THE INVENTION

Accordingly, the present invention is directed to an electrochemical cell having plate electrodes housed inside mating "clam shell" casing components. Also, the present casing design allows for indentation structures in the casing components by virtue of them being stamped metal parts. Depending on the design, some of these indentations are not possible with traditional cylindrical and prismatic casing designs. When mated together, the casing components are form-fitting with respect to the internal battery structure so as to reduce the overall size of the electrochemical package. This provides the cell with the greatest amount of energy per unit size.

The foregoing and additional advantages and characterizing features of the present invention will become clearly apparent upon reading of the ensuing description together with the included drawings wherein:

BEST MODE FOR CARRYING OUT THE INVENTION

Figure 1:
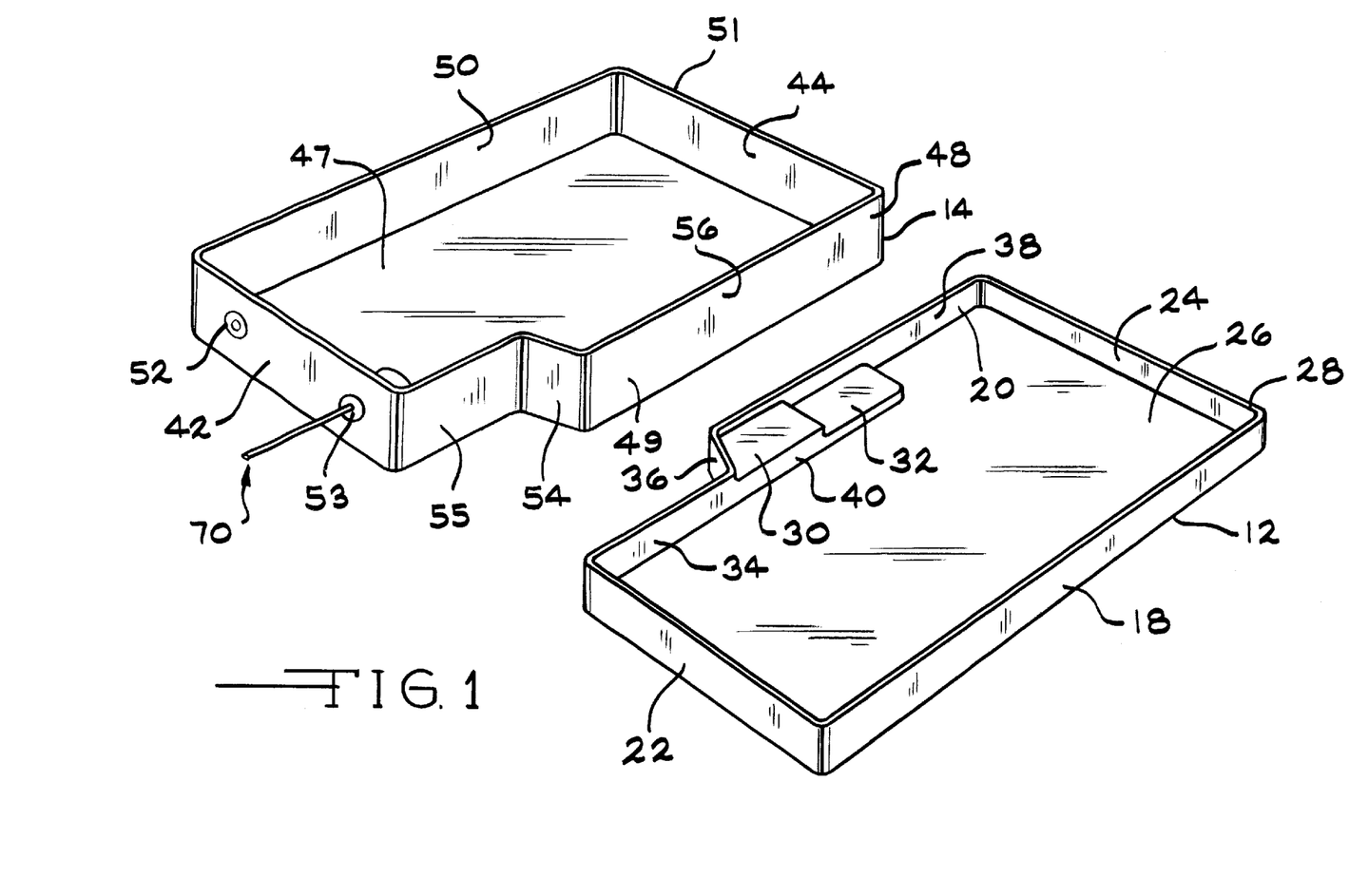
FIG. 1 is a perspective view showing an embodiment depicting two halves of a electrochemical cell casing.
Figure 2:
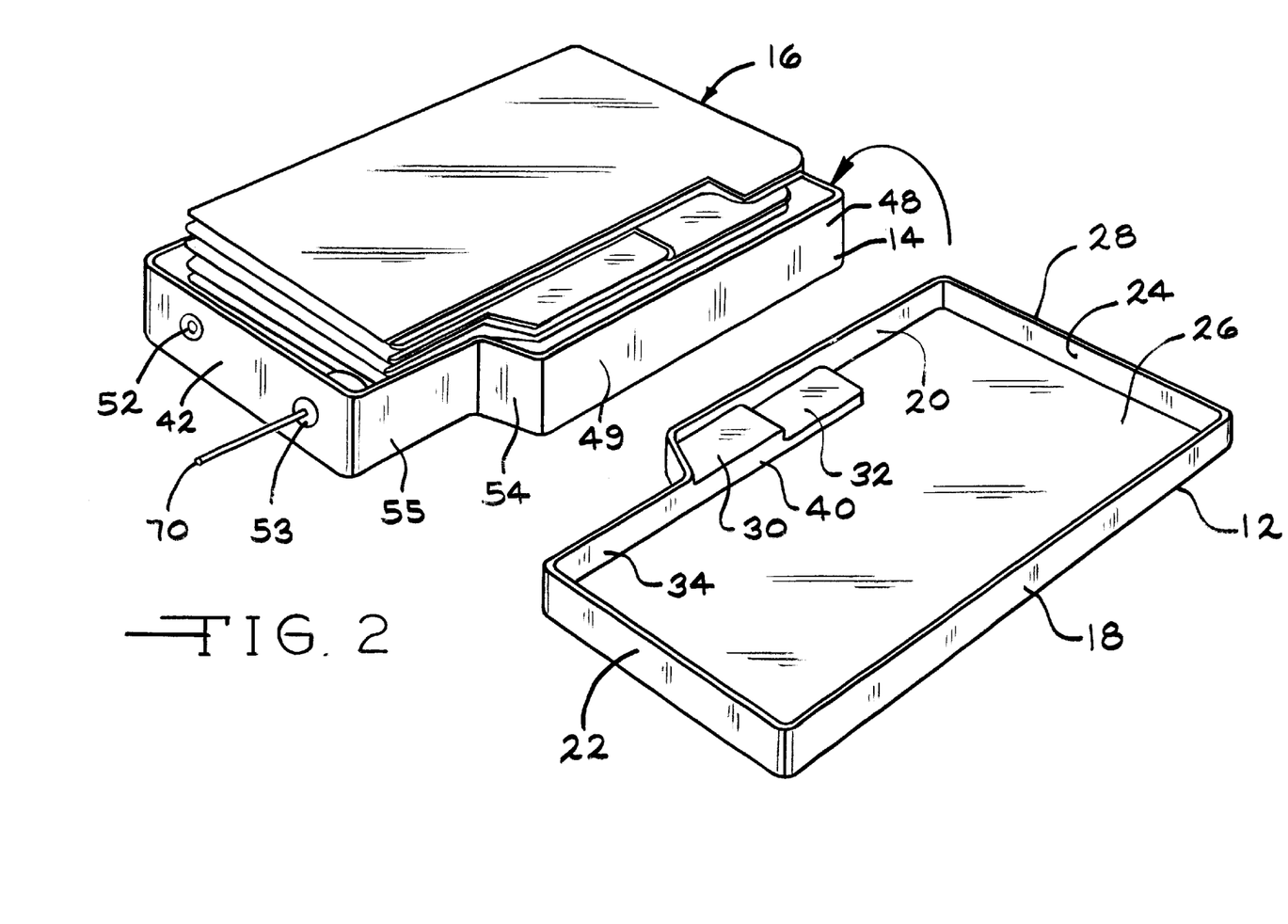
FIG. 2 depicts an embodiment of the cell casing, the lower portion containing the electrode assembly.
Figure 3:
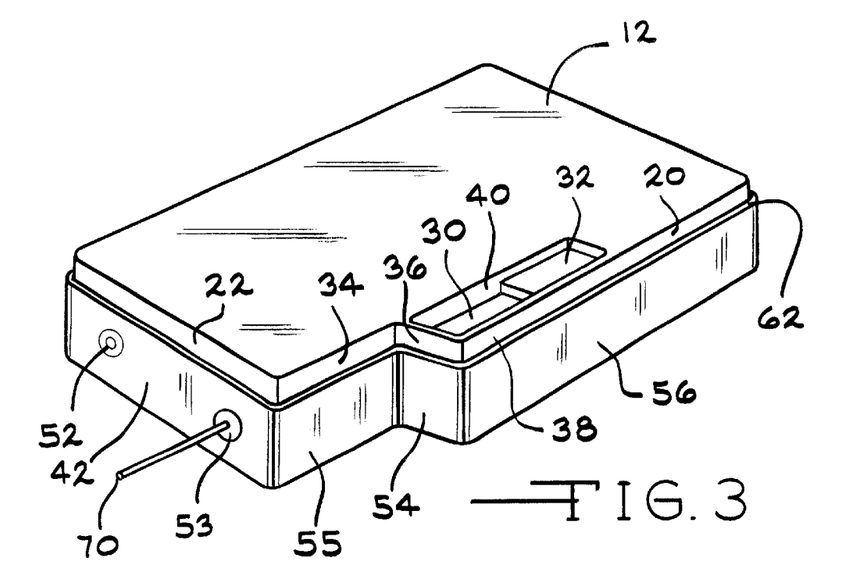
FIGS. 3 and 4c depict assembled embodiments of the electrochemical cell.
Figure 4A:
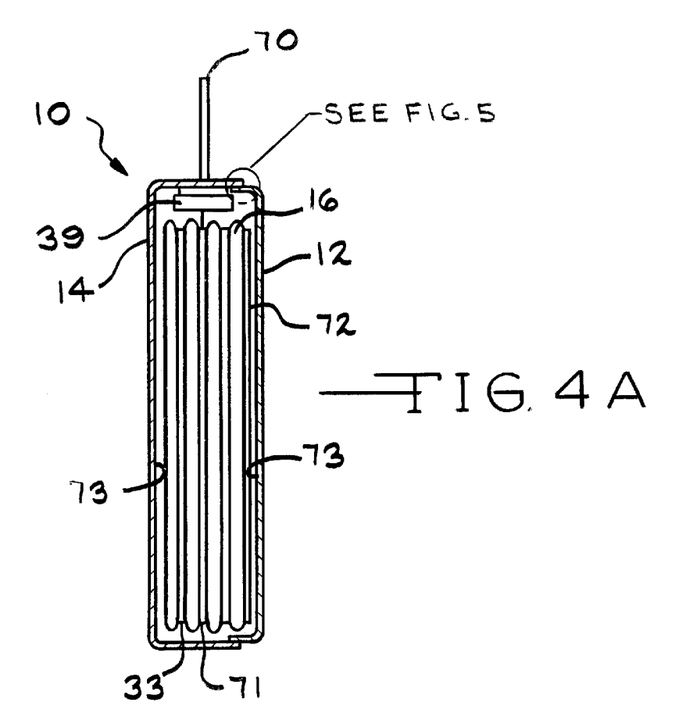
FIGS. 4a and 4b show sectional elevations of methods of assembly of embodiments of the two stamped metal halves.

Turning now to the drawings, FIGS. 1 to 4a illustrate an electrochemical cell 10 according to the present invention. The cell 10 includes a conductive casing of metal, such as stainless steel, having first and second clam shell portions 12 and 14. As shown in FIG. 4, the clam shell portions 12 and 14 are mated together and sealed about their periphery to provide a hermetic enclosure for an electrode assembly 16 (FIGS. 2 and 4a).

In particular, the first clam shell 12 comprises spaced apart side walls 18 and 20 extending to and meeting with spaced apart end walls 22 and 24. The side walls 18, 20 and the end walls 22, 24 meet each other at rounded corners and extend to a front wall 26. Opposite the front wall 26 is an continuous edge 28 of side walls 18, 20 and end walls 22, 24.

End wall 24 has a greater length than end wall 22. The difference in length between these walls accommodates a plurality of step portions 30 and 32. In this manner, side wall 20 include a first portion 34 extending from end wall 22 and forming into an angled side wall portion 36 which meets a second portion 38 extending to end wall 24. Recessed below the edge 28 and partially bordered by the angled side wall 36 and the second portion 38 of the side wall 20 is the major surface of the first step 30 which in turn leads to the second step 32. The major surface of the second step 32 is spaced further from the edge 28 than the major surface of the first step 30. The second step 32 ends at the front wall 26. The stepped portion of the first clam shell 12 is completed by an extension portion 40 of the first portion 34 of side wall 20. The extension portion 40 has a shape similar to the steps 30 and 32 and ends at the front wall.

The second clam shell 14 comprises spaced apart side walls 49 and 50 extending to and connecting with spaced apart end walls 42 and 44. The side walls 49 and 50 and end walls 42 and 44 meet at rounded corners and extend to front wall 47. Opposite the front wall is a continuous edge 51 of the side walls 49 and 50 and end walls 42 and 44. End wall 44 has a greater length than end wall 42. In this manner, side wall 49 includes a first portion 55 extending from end wall 42 and forming into an angled side wall portion 54 which meets a second portion 50 of side wall 49 extending to the end wall 44.

Figure 5:
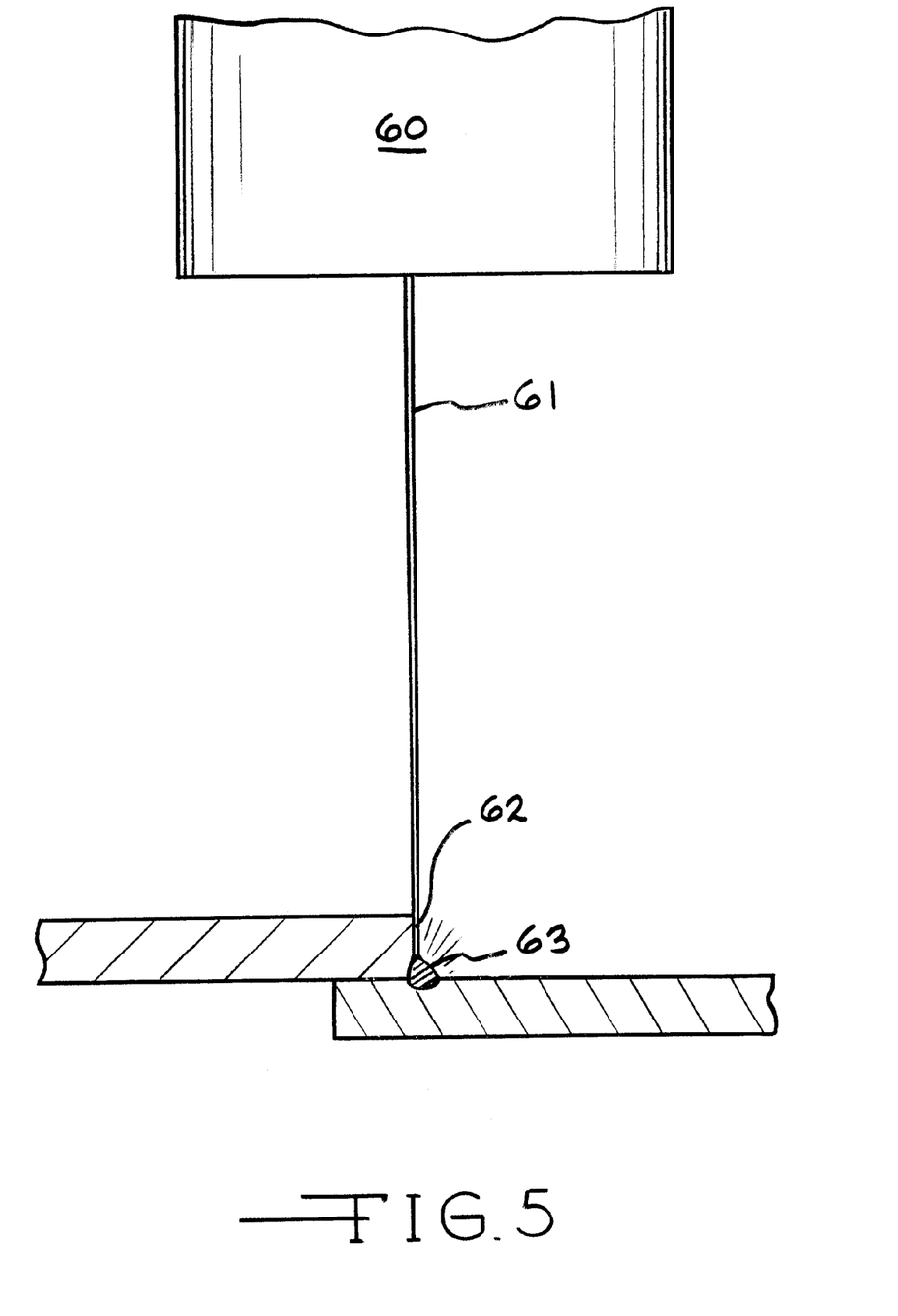
FIG. 5 depicts the welding detail of an embodiment of the clam shell halves peripheral mating seam.

In one preferred embodiment of the present invention shown in FIGS. 3, 4a, and 5, the first clam shell 12 is sized to fit inside the periphery of the second clam shell 14 in a closely spaced relationship. This means that side wall 18 is somewhat shorter than side wall 50, end wall 22 is somewhat shorter than side wall 42, side wall 20 is somewhat shorter than side wall 49 and end wall 24 is somewhat shorter than end wall 44. Also, the first and second portions 34 and 38 of side wall 20 are sized to be received inside the first and second portions 55 and 50 of side wall 49 with the intermediate angled side wall portion 36 of side wall 20 aligned with and received inside of the intermediate angled side wall portion 54 of side wall 49.

In the embodiment of the present invention shown in FIG. 3, the first clam shell 12 is received and nested inside the second clam shell 14 in a closely spaced relationship. This figure clearly shows the first step 30 and the second step 32 recessed into the front wall 26 of the first clam shell 12. In particular, the first step 30 is surrounded and defined by the angled side wall 36, the second portion 38 of side wall 20, an offset 43 leading to the second step 32 and the extension portion 40. Similarly, the second step 32 is defined by the second portion 38 of side wall 20, a back wall 37 extending from portion 38 and leading to the extension 40.

In the embodiment shown, the first and second steps 30 and 32 of the recesses are generally parallel to the major surface of front wall 26. However, this is not necessary to practice the present invention. Instead, the recess may have virtually any shape as long as it is confined to the body of the clam shell 12 including walls 18, 20, 22 and 24. In that respect, the walls 36, 38, 43 and 40 surrounding the first step 30, and the walls 38, 37, 38 and 40 surrounding the second step 32 need not be at a perpendicular angle with respect to the respective steps and the front wall 26 of the clam shell 12. Instead, they may be at an obtuse angle or a combination of perpendicular and obtuse angles.

Thus, the steps 30 and 32 are recessed into the front wall 26 of the first clam shell 12, bordered by walls on all sides. The steps 30 and 32 are provided in the front wall 26 of the first clam shell 12 for the purposed of received a component (not shown) of the device intended to be powered by the electrochemical cell housed inside the casing. The casing constructions known in the prior art do not provide for such recessed structure. Both the conventionally known cylindrical case and the prismatic case are deep drawn structures that do not allow for a recessed structure being provided therein without compromising the integrity of the deep drawn container. As those skilled in the art can also see other embodiments of the current invention can be practiced in the absence of recesses or indentations in one or both of the metal stamped mated stamped metal halves.

In that respect, the mating clam shells 12 and 14 of the present invention are stamped or otherwise formed from sheet metal. This construction technique readily allows the provision of recessed structures into the major front wall 26 of the first clam shell. However, it should be readily apparent to those skilled in the art that the shape, size and exact positioning of the recessed steps 26 and 28 in the first clam shell is by way of example only. In a broader sense, either one of the first and second clam shells 12 and 14 can have a plurality of recesses formed into their respective major front walls 26 and 47 any where within their surface area. This provides for greater flexibility in adapting a cell casing to a particular application. For example, if the cell is intended to power an implantable medical device and the manufacturer requires that a component of the device be nested within the major face of one of the clam shells 12 and 14, the recess structure of the present invention provides for this.

FIG. 5 depicts welding of clam shell halves 12 and 14 at peripheral seam 62 formed by mating continuous edges 28 and 51. Weld 63 is created by laser 61 from welding source 60.

Figure 6:
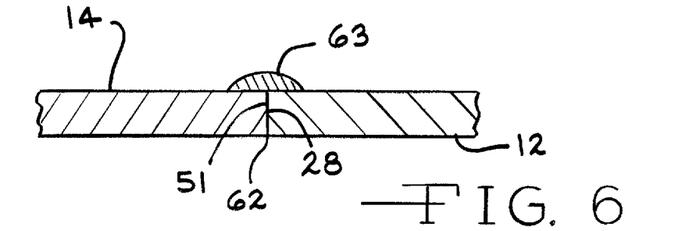
FIGS. 6 through 10 depicts details of various embodiments of continuous peripheral mating seams for welding.

In FIG. 6, peripheral seam 62 is created by positioning continuous peripheral edge 51 of clam shell half 14 with continuous peripheral edge 28 of shell half 12 in a coplanar arrangement for weld 63.

Figure 7:
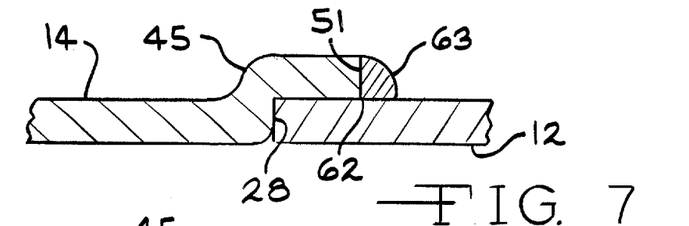

In FIG. 7, clam shell half 14 contains an outwardly extending offset or stepped portion 45 at the clam shell periphery near continuous edge 51. The offset distance is equal to the thickness of the walls 18, 20, 22 and 24 forming the continuous edge 28. During construction of the casing, clam shell half 12 is partially disposed inside clam shell half 14. Weld 63 is then provided at the seam 62 created by contacting the continuous edge 51 with the upper surface 59 of clam shell 12 to provide a continuous hermetic seal there.

Figure 8:
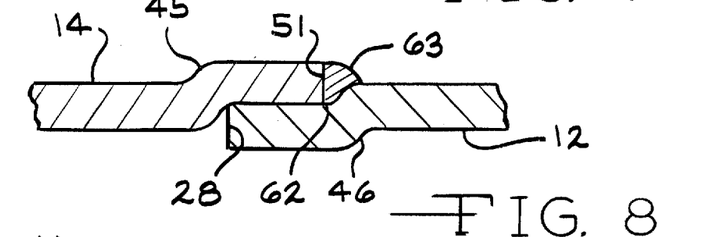

In FIG. 8, clam shell half 14 contains an outwardly extending continuous offset or stepped portion 45 on the periphery near continuous edge 51 and clam shell half 12 contains an inwardly extending continuous offset or stepped portion 46 on the periphery near continuous edge 28. The offset distances are equal to one-half the thickness of the various walls forming the continuous edges 28 and 51. When the clam shells 12 and 14 are mated together, the oppositely extending stepped portions 45 and 46 result in clam shell half 12 being partially disposed inside clam shell half 14 in a non-coplanar arrangement. Weld 63 is then provided at the seam 62 created by contacting the continuous edge 51 with the upper surface 59 of clam shell 12 to provide continuous hermetic seal.

Figure 9:
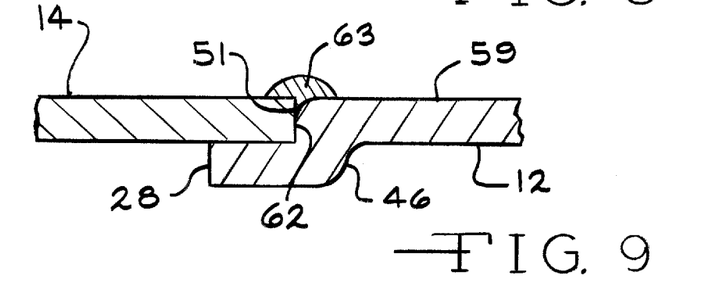

In FIG. 9, clam shell half 12 contains an inwardly extending offset or stepped portion 46 at the clam shell periphery near continuous edge 28. The offset distance is equal to the thickness of the walls 42, 44, 49 and 50 forming the continuous edge 51. During construction of the casing, clam shell half 12 is partially disposed inside of clam shell half 14. With this construction, the continuous edge 51 of clam shell 14 butts against clam shell 12 with weld 63 providing a hermetic seal at edge 51 with the upper surface 59 of shell 12.

Figure 10:
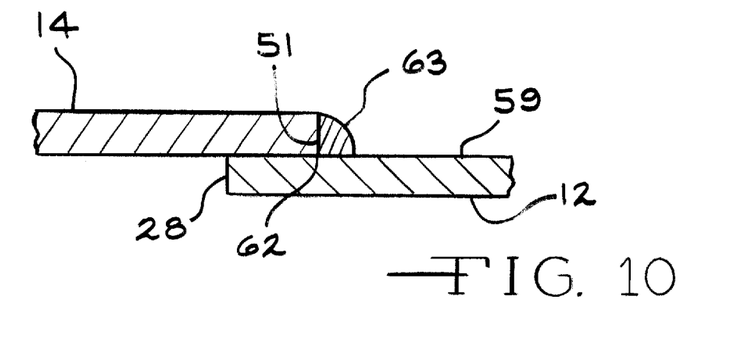

In FIG. 10, peripheral seam 62 is created by lapping continuous edge 51 of clam shell 14 over continuous edge 28 of clam shell 12. In this embodiment, clam shell 12 is partially disposed inside clam shell 14 in a non-coplanar arrangement. Again, weld 63 provides a hermetic seal at the continuous seam 62 formed at the mating of edge 51 with upper surface 59 of shell 12.

The casing of the present invention is readily adapted for housing various types of electrochemical chemistries such as alkali metal/solid cathode or alkali metal/oxyhalide electrochemical cells of both the solid cathode and liquid cathode types. The exemplary electrochemical cell 16 housed in the casing of the present invention is of the liquid electrolyte type comprised of a cathode electrode having a body 33 of solid cathode material in the form of plate 39 pressed together and bonded against a cathode current collector. The cathode active material is preferably comprised of a metal, a metal oxide, a mixed metal oxide or a metal sulfide, and the cathode current collector is fabricated from a thin sheet of metal. Suitable materials for the current collector include nickel, aluminum, stainless steel, mild steel and titanium.

The benefit of having a lap joint construction to the mating clam shells 12 and 14 of the present casing (FIGS. 7 to 10) is to prevent the laser beam 61 from compromising the cell components housed inside the casing. With the construction shown in FIG. 6, it is possible for the laser beam welding the clam shells 12 and 14 together to penetrate past the junction of peripheral edge 51 to the electrode assembly housed therein. This could lead to compromise of the electrode assembly. For that reason, a backing ring (not shown) is typically used in welding the casing configuration of FIG. 6.

The embodiment depicted in FIGS. 2 and 4a shows an electrolyte fill opening 52 contained in side wall 42, a glass-to-metal seal 53, and a cathode terminal lead 70.

Cell 10 further includes an anode electrode, generally designated 71. The anode electrode comprises an anode active material, such as lithium pressed to the opposite sides of an anode current collector. The anode current collector is fabricated from a thin sheet of metal such as nickel.

The anode electrode 71 is in operative contact with the cathode plate 32 through a thin sheet of separator material 72. The separator surrounds and envelopes the cathode body 33 to prevent direct physical contact with the anode 71.

The terminal lead 70 connected to the cathode current collector extends through a header assembly comprising the glass-to-metal seal 53 fitted in the end wall 42 of clam shell 14. Lead 70 is the positive electrical terminal, being connected to the cathode electrode 33. The anode electrode 71 is in operative contact with the conductive casing through direct physical contact of the anode active material with the clam shells 12, 14. The cathode current collector is of titanium and terminal lead 70 is of molybdenum, separators 72 and 73 are of polypropylene. The activating electrolyte is a 1.0M to 1.4M solution of $LiAsF_6$ or $LiPF_6$ in a 50:50 mixture of, by volume, 1,2-dimethoxyethane and propylene carbonate. Glass seal 53 is of TA-23 Hermetic sealing glass, while the casing clam shells 12, 14 are of stainless steel.

This electrochemical system is of a primary cell type. However, those skilled in the art will readily recognize that the casing of the present invention is readily adopted to house both primary electrochemical systems of either a solid cathode or liquid catholyte type, or a secondary cell such as a lithium ion cell having a carbonaceous negative electrode and lithium cobalt oxide positive electrode.

Figure 4B:
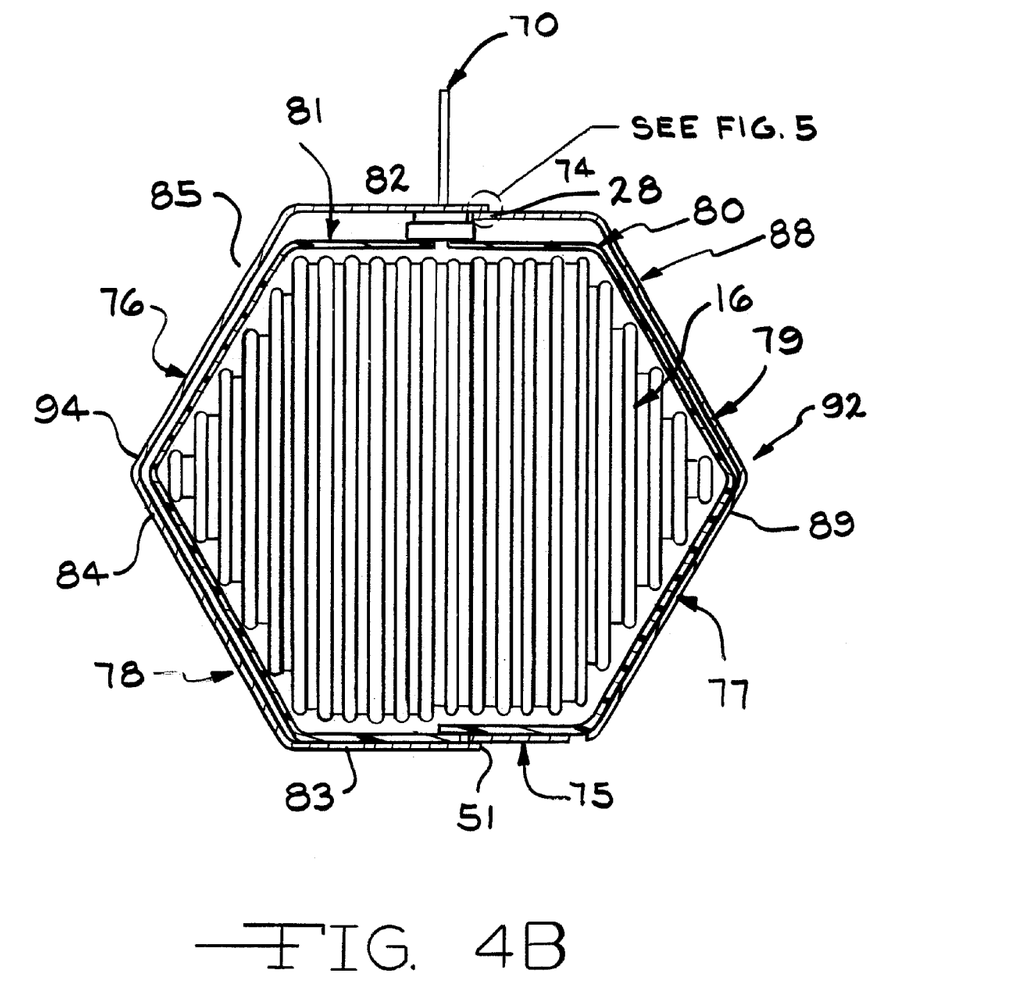

It is not necessary that the casing have a rectangular cross section. For example, FIG. 4b shows an embodiment of a hexagonally shaped cross section. Although a hexagonal shape is shown, it can be appreciated by those skilled in the art, that a number of geometrical shapes can be used and a hexagon is shown for illustrative purposes only.

In this embodiment, clam shell 92 is coplanar with clam shell 94 about the horizontal axis so that shell 92 fits inside the periphery of shell 94. Thus, side walls 77 and 79 are somewhat shorter than side walls 76 and 78, and side walls 74 and 75 are somewhat shorter than side walls 82 and 83.

Figure 4C:
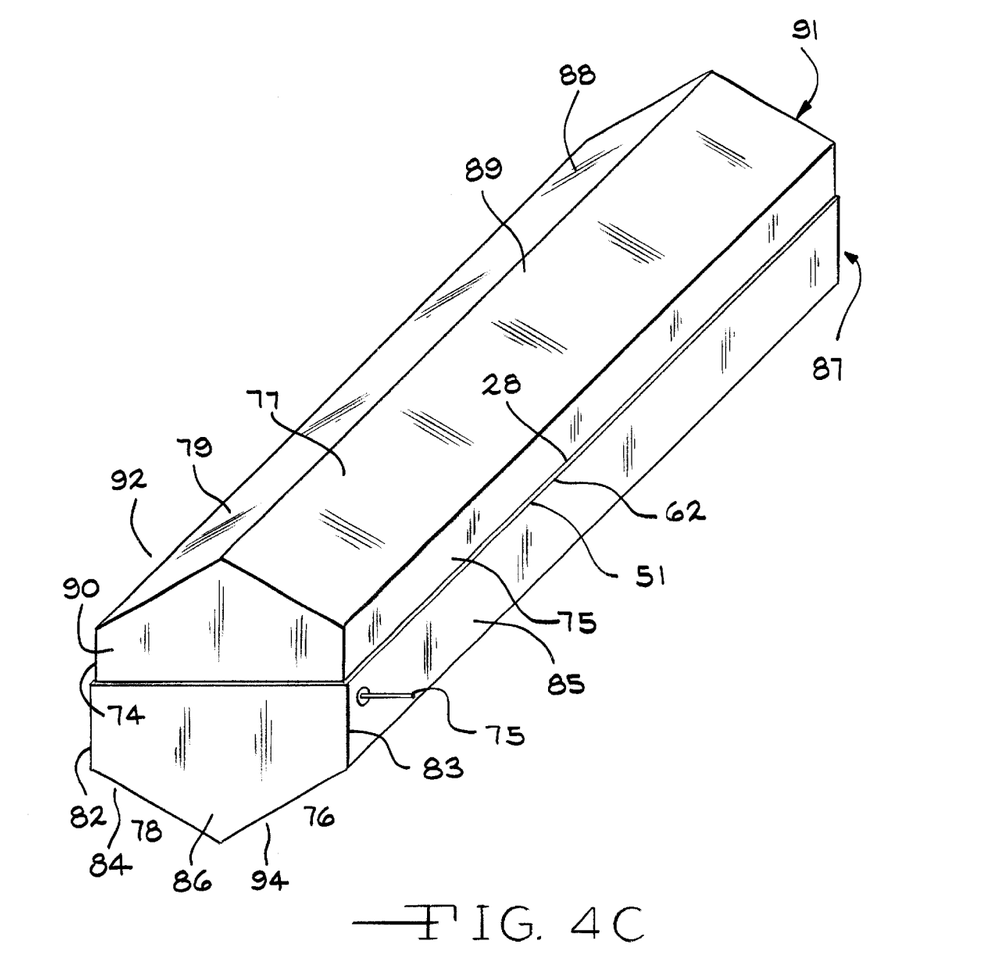

Furthermore, it will be readily apparent to those skilled in the art that the walls of the hexagonally shaped cross section shell halves terminate in equally spaced end walls defined by the junction of the side walls meeting at rounded edges. Specifically, clam shell half 94 is defined by walls 76 and 78, equal in length and emanating from an acute angle of 60°, each extending to and meeting walls 82 and 83 respectively, with rounded edges at an angle of 60°. Walls 82 and 83 are equal in length and extend from wall surfaces 85 and 84, respectively, up to continuous edge 51 formed by the junction of end walls 86 and 87 and side walls 82 and 83. Clam shell half 92 is defined by walls 77 and 79, equal in length and both emanating from an acute angle of 60°, each extending to and meeting with walls 74 and 75 respectively, with rounded edges at an angle of 60°. Walls 74 and 75 are equal in length and extend from wall surfaces 88 and 89 up to continuous edge 28 formed by the junction of side walls 74 and 75 and end walls 90 and 91 (FIG. 4c).

To manufacture the case it is necessary to appropriate the proper sheet thickness conductive metal and draw the individual halves by stamping or other such suitable means. The peripheral edges need to be trimmed, ensuring weld-ready continuous peripheral edges. The glass-metal seal with terminal lead 70 is installed in the clam shall 14 the lower drawn metal half. The electrode assembly is installed in the clam shell 14 which is then mated with the first clam shell 12. The edges of the mated clam shells 12, 14 form a continuous peripheral surface, which, as previously described with respect to FIGS. 6 to 10, is sealed by welding, creating a hermetically sealed electrochemical cell.

Use of the two stamped metal component configuration for the manufacture of the implantable grade lithium anode based electrochemical cells permits optimum utilization of available volume in an implantable medical device, yielding greater packaging efficiencies in smaller devices. The result is a highly efficient power source. Heretofore, the manufacturing process required many more steps to create a hermetically sealed cell capable of being implanted. The invention will enhance the art by decreasing manufacturing costs.

While preferred embodiments of the present invention have been disclosed, it will be appreciated that it is not limited thereto, but may be otherwise embodied with the scope of the following claims.

I claim:

1. An electrochemical cell, which comprises:
    a) an anode;
    b) a cathode;
    c) an electrolyte activating the anode in electrochemical association with the cathode; and
    d) a casing, which comprises:
        i) a first casing member having a first surrounding side wall extending to and meeting with a continuous first major face wall;
        ii) a second casing member having a second surrounding side wall extending to and meeting with a continuous second major face wall;
        iii) wherein the first casing member and the second casing member are of a metallic material and matable to each other; and iv) wherein in the mated relationship, a first outer edge of the first surrounding side wall faces the second major face wall and a second outer edge of the second surrounding side wall faces the first major face wall with at least a portion of the first surrounding side wall in an overlapping, direct contact relationship with at least a portion of the second surrounding side wall to form a seam for sealing the first and second casing members together, thereby enabling the casing to house the anode, the cathode and the electrolyte contained therein.

2. The electrochemical cell of claim 1 wherein at least one of the first surrounding side wall and the second surrounding side wall is angled other than in a normal relationship with respect to the first major face wall and the second major face wall, respectively.

3. The electrochemical cell of claim 1 wherein at least one of the first and second major face walls is planar.

4. The electrochemical cell of claim 1 wherein at least one of the first and second major face walls is provided with a recess spaced inwardly toward the first and second edges of the respective first and second surrounding side walls.

5. The electrochemical cell of claim 4 wherein the at least one recess comprises a recess side wall at least partly formed by one of the first and the second surrounding side walls of the respective first and second casing members.

6. The electrochemical cell of claim 1 wherein each of the continuous first and second major face walls is substantially planer and they are disposed parallel to each other with the first casing member and the second casing member mated to each other.

7. The electrochemical cell of claim 1 wherein each of the continuous first and second major face walls is substantially planer and they are angled with respect to each other in a non-parallel relationship with the first casing member and the second casing member mated to each other.

8. The electrochemical cell of claim 1 as either a primary cell of a lithium/silver vanadium oxide couple or a secondary cell of a carbonaceous negative electrode and a lithium cobalt oxide positive electrode.

9. The electrochemical cell of claim 1 wherein there is at least one recess in each of the first and second portions of the casing.

10. The electrochemical cell of claim 1 wherein a proximal first side wall portion of the first surrounding side wall immediately adjacent to the first major face wall is disposed in a generally normal relationship therewith and a distal first side wall portion extending from the proximal first side wall portion is offset such that the distal first side wall portion is in an overlapping relationship with at least a portion of the second surrounding side wall when the second casing member is mated with the first casing member.

11. The electrochemical cell of claim 1 wherein a proximal first side wall portion of the first surrounding side wall immediately adjacent to the first major face wall is disposed in a generally normal relationship therewith and a distal first side wall portion extending from the proximal first side wall portion is offset inwardly with respect to the proximal first side wall portion and wherein a proximal second side wall portion of the second surrounding side wall immediately adjacent to the second major face wall is disposed in a generally normal relationship therewith and a distal second side wall portion extending from the proximal second side wall portion is offset outwardly with respect to the proximal second side wall portion such that when the first casing member is mated to the second casing member, the inwardly extending offset of the distal first side wall portion is overlapped by the outwardly extending offset of the distal second side wall portion to form the seam for welding.

12. The electrochemical cell of claim 11 wherein the proximal first side wall portion of the first surrounding side wall and the proximal second side wall portion of the second surrounding side wall are generally aligned in a coplanar relationship when the first casing member is mated with the second casing member.

13. The electrochemical cell according to claim 1 wherein the first casing member and the second casing member are characterized as having been sealed together using a laser beam.

14. A method for providing an electrochemical cell, comprising the steps of:
   a) forming first casing member having a first surrounding side wall extending to and meeting with a continuous first major face wall and a second casing member having a second surrounding side wall extending to and meeting with a continuous second major face wall, wherein the first and second casing members are of a metallic material;
   b) positioning an anode and a cathode in one of the first and the second casing members;
   c) connecting the anode and the cathode to respective terminals;
   d) mating the first casing member to the second casing member with a first outer edge of the first surrounding side wall facing the second major face wall and a second outer edge of the second surrounding side wall facing the first major face wall such that at least a portion of the first surrounding side wall overlaps and is in direct contact with at least a portion of the second surrounding side wall to house the anode and the cathode therein;
   e) sealing the overlapping first surrounding side wall to the second surrounding side wall; and
   f) activating the anode and the cathode with an electrolyte.

15. The method of claim 14 including providing at least one of the first surrounding side wall and the second surrounding side wall being angled other than in a normal relationship with respect to the first major face wall and the second major face wall, respectively.

16. The method of claim 14, including providing at least one of the first and second major face walls being planar.

17. The method of claim 14 including providing at least one of the first and second major face walls having a recess spaced inwardly toward an edge of the respective first and second surrounding side walls.

18. The method of claim 17, including providing the at least one recess comprising a recess side wall at least partly formed by one of the first and the second surrounding side walls of the respective first and second casing members.

19. The method of claim 14 including providing each of the continuous first and second major face walls being substantially planar and disposed parallel to each other with the first casing member and the second casing member mated to each other.

20. The method of claim 14, including providing each of the continuous first and second major face walls being substantially planar and angled with respect to each other in a non-parallel relationship with the first and the second casing members mated to each other.

21. The method of claim 14 including providing the cell as either a primary cell of a lithium/silver vanadium oxide couple or a second electrochemical cell of a carbonaceous negative electrode and a lithium cobalt oxide positive electrode.

22. The method of claim 14 including providing at least one recess in each of the first and second portions of the casing.

23. The method of claim 14 including providing a proximal first side wall portion of the first surrounding side wall immediately adjacent to the first major face wall being disposed in a generally normal relationship therewith and a distal first side wall portion extending from the proximal first side wall portion being offset such that the distal first side wall portion is in an overlapping relationship with at least a portion of the second surrounding side wall when mating the second casing member with the first casing member.

24. The method of claim 14 including providing a proximal first side wall portion of the first surrounding side wall immediately adjacent to the first major face wall in a generally normal relationship therewith and a distal first side wall portion extending from the proximal first side wall portion being offset inwardly with respect to the proximal first side wall portion and further providing a proximal second side wall portion of the second surrounding side wall immediately adjacent to the second major face wall in a generally normal relationship therewith and a distal second side wall portion extending from the proximal second side wall portion being offset outwardly with respect to the proximal second side wall portion such that when mating the first casing member to the second casing member, the inwardly extending offset of the distal first side wall portion is overlapped by the outwardly extending offset of the distal second side wall portion to house the anode and the cathode therein.

25. The method of claim 24, including aligning the proximal first side wall portion of the first surrounding side wall and the proximal second side wall portion of the second surrounding side wall in a generally coplanar relationship when mating the first casing member with the second casing member.

26. The method of claim 14, including welding the first casing member to the second casing member to seal them together.

27. The electrochemical cell of claim 10 wherein the proximal first side wall portion of the first surrounding side wall and the second surrounding side wall are generally aligned in a coplanar relationship when the first casing member is mated with the second casing member.

28. The electrochemical cell of claim 1 wherein the first surrounding side wall of the first casing member is disposed completely inwardly of the second surrounding side wall of the second casing member with the first and second casing members mated to each other.

29. The method of claim 23 including providing the proximal first side wall portion of the first surrounding side wall and the proximal second side wall portion of the second surrounding side wall being generally aligned in a coplanar relationship when mating the first casing member with the second casing member.

30. The method of claim 14 including disposing the first surrounding side wall of the first casing member completely inwardly of the second surrounding side wall of the second casting member when mating the first and second casing members to each other.

31. An electrochemical cell, which comprises:
a) an anode;
b) a cathode;
c) an electrolyte activating the anode in electrochemical association with the cathode; and
d) a casing, which comprises:
  i) a first casing member having a first surrounding side wall extending to and meeting with a continuous first major face wall, wherein the first surrounding side wall has a first height measured from the first major face wall to a first outer edge of the first surrounding side wall;
  ii) a second casing member having a second surrounding side wall extending to and meeting with a continuous second major face wall, wherein the second surrounding side wall has a second height measured from the second major face wall to a second outer edge of the second surrounding side wall;
  iii) wherein the first casing member and the second casing member are of a metallic material and matable to each other; and
  iv) wherein in the mated relationship, the first outer edge of the first surrounding side wall faces the second major face wall and the second outer edge of the second surrounding side wall faces the first major face wall with the first height of the first surrounding side wall being greater than the second height of the second surrounding side wall such that a portion of the first surrounding side wall is in an overlapping, direct contact relationship with at least a portion of the second surrounding side wall to form a seam there for securing the first and second casing members together, thereby enabling the casing to house the anode, the cathode and the electrolyte contained therein.

32. An electrochemical cell, which comprises:
a) a casing, which comprises:
  i) a first casing member having a first surrounding side wall extending to and meeting with a continuous first major face wall;
  ii) a second casing member having a second surrounding side wall extending to and meeting with a continuous second major face wall;
  v) wherein the first casing member and the second casing member are of a metallic material and matable to each other; and
  vi) wherein in the mated relationship, a first outer edge of the first surrounding side wall faces the second major face wall and a second outer edge of the second surrounding side wall faces the first major face wall with at least a portion of the first surrounding side wall in an overlapping, direct contact relationship with at least a portion of the second surrounding side wall; and
b) an anode and a cathode housed in the casing comprising the first casing member and the second casing member having their respective first and second surrounding side walls mated to each other to form a seam;
c) a weld at the seam securing the first casing member to the second casing member, thereby enabling the casing to house the anode and the cathode contained therein;
d) an electrolyte filled in the casing and activating the anode in electrochemical association with the cathode; and
e) a first terminal for the anode and a second terminal for the cathode, wherein the casing serves as one of the first and second terminals and the other of the terminals is insulated from the casing.

33. A casing for housing an electrochemical cell, the casing comprising:
a) a first casing member having a first surrounding side wall extending to and meeting with a continuous first major face wall;

a) a first casing member having a first surrounding side wall extending to and meeting with a continuous first major face wall, wherein the first surrounding side wall has a first height measured from the first major face wall to a first edge of the first surrounding side wall;

b) a second casing member having a second surrounding side wall extending to and meeting with a continuous second major face wall, wherein the second surrounding side wall has a second height measured from the second major face wall to a second edge of the second surrounding side wall;

c) wherein the first casing member and the second casing member are of a metallic material and matable to each other; and d) wherein n the mated relationship, a first outer edge of the first surrounding side wall faces the second major face wall and a second outer edge of the second surrounding side wall faces the first major face wall with the first height of the first surrounding side wall being greater than the second height of the second surrounding side wall such that a portion of the first surrounding side wall is in an overlapping, direct contact relationship with at least a portion of the second surrounding side wall to form a seam there for securing the first and second casing members together, thereby enabling the casing to form the housing.

b) a second casing member having a second surrounding side wall extending to and meeting with a continuous second major face wall;

c) wherein the first casing member and the second casing member are of a metallic material and d) matable to each other; and wherein in the mated relationship, a first outer edge of the first surrounding side wall faces the second major face wall and a second outer edge of the second surrounding side wall faces the first major face wall with a portion of the first surrounding side wall in an overlapping, direct contact relationship with at least a portion of the second surrounding side wall to form a seam for sealing the first and second casing members together, thereby enabling the casing to form the housing.

34. The casing of claim 33 wherein at least one of the first and second casing members has at least one opening provided therein.

35. The casing of claim 33 wherein at least one of the first and second surrounding side walls has at least one opening provided therein intended as either an electrolyte fill opening or a terminal lead opening for the cell.

36. The casing of claim 33 where in at least one of the first and second surrounding side walls has a first opening intended as an electrolyte fill opening and a second opening intended as a terminal lead opening.

37. A casing for housing an electrical energy storage device, the casing comprising:

* * * * *

UNITED STATES PATENT AND TRADEMARK OFFICE
CERTIFICATE OF CORRECTION

PATENT NO. : 6,613,474 B2
DATED : September 2, 2003
INVENTOR(S) : Frustaci et al.

It is certified that error appears in the above-identified patent and that said Letters Patent is hereby corrected as shown below:

Column 7,
Line 8, insert the word -- hermetically -- after "seam for".
Line 41, delete "1" and insert -- 4 -- and delete "there is" and insert -- the --.
Lines 42 to 43, delete "in each of the first and second portions of the casing" and insert -- has a substantially planar recess face --.

Column 8,
Line 35, insert the word -- hermetically -- before "sealing the overlapping".

Column 9,
Line 1, delete "14" and replace with -- 17 -- and insert the word -- the -- after "providing".
Lines 2 and 3, delete "in each of the first and second portions of the casing" and insert the words -- having a substantially planar recess face --.

Column 10,
Line 26, insert the word -- hermetically -- after "to form a seam there for".
Line 37, delete "v)" and insert -- iii) --.
Line 40, delete "vi)" and insert -- iv) --.
Line 52, insert the word -- hermetically -- after "at the seam".

Column 11,
Line 13, insert the word -- hermetically -- after "to form a seam for".

Column 12,
Line 24, insert the word -- hermetic -- after "side wall to form a".

Signed and Sealed this

Sixteenth Day of December, 2003

JAMES E. ROGAN
*Director of the United States Patent and Trademark Office*